US00PP23626P2

(12) United States Plant Patent
de Kroon

(10) Patent No.: US PP23,626 P2
(45) Date of Patent: May 21, 2013

(54) *DIASCIA* PLANT NAMED 'DISZ0001'

(50) Latin Name: *Diascia barberae*
Varietal Denomination: DISZ0001

(75) Inventor: Marnix de Kroon, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 92 days.

(21) Appl. No.: 13/200,892

(22) Filed: Oct. 4, 2011

(51) Int. Cl.
*A01H 5/00* (2006.01)

(52) U.S. Cl.
USPC ..... Plt./425

(58) Field of Classification Search ..... Plt./425
See application file for complete search history.

*Primary Examiner* — Susan McCormick Ewoldt
(74) *Attorney, Agent, or Firm* — Joshua L. Price

(57) ABSTRACT

A new *Diascia* plant named 'DISZ0001' particularly distinguished by the relatively large, deep red flowers, medium to deep green foliage, strong and freely branching, and a medium sized, semi-upright plant habit.

1 Drawing Sheet

Latin name of the genus and species of the plant claimed: *Diascia barberae.*

Varietal denomination: 'DISZ0001'.

BACKGROUND OF THE NEW PLANT

The present invention comprises a new *Diascia*, botanically known as *Diascia barberae*, and hereinafter referred to by the variety name 'DISZ0001'.

'DISZ0001' is a product of a planned breeding program. The new cultivar 'DISZ0001' has relatively large, deep red flowers, medium to deep green foliage, strong and freely branching, and a medium sized, semi-upright plant habit.

'DISZ0001' originated from a hybridization made in May 2006 in a controlled breeding program in Enkhuizen, Netherlands. The female parent was an unpatented, proprietary plant designated 'H0026-3', with red flowers, has fewer branches, darker green foliage, is a few days later to flower.

The male parent of 'DISZ0001' was an unpatented, proprietary plant designated 'D29', with lighter red, slightly larger flowers, with fewer branches.

The resulting seeds were sown in February 2007. 'DISZ0001' was selected as one flowering plant within the progeny of the stated cross in May 2007 in a controlled environment in Enkhuizen, Netherlands.

The first act of asexual reproduction of 'DISZ0001' was accomplished when vegetative cuttings were propagated from the initial selection in May 2007 in a controlled environment in Enkhuizen, Netherlands.

BRIEF SUMMARY OF INVENTION

Horticultural examination of plants grown from cuttings of the plant initiated in the spring of 2008 in Andijk and Enkhuizen, Netherlands, and continuing thereafter, has demonstrated that the combination of characteristics as herein disclosed for 'DISZ0001' are firmly fixed and are retained through successive generations of asexual reproduction.

'DISZ0001' has not been observed under all possible environmental conditions. The phenotype may vary significantly with variations in environment such as temperature, light intensity and day length.

Plant Breeder's Rights for this cultivar have been applied in Canada on Dec. 24, 2010, #10-7137 and at the Community Plant Variety Office on Oct. 7, 2010, #2010/2108. 'DISZ0001' has not been made publicly available more than one year prior to the filing of this application.

The following traits have been repeatedly observed and are determined to be basic characteristics of the new variety. The combination of these characteristics distinguishes this *Diascia* as a new and distinct variety.

BRIEF DESCRIPTION OF THE PHOTOGRAPHS

The accompanying photographic drawing shows typical flower and foliage characteristics of 'DISZ0001' with colors being as true as possible with an illustration of this type.

Figure 1:
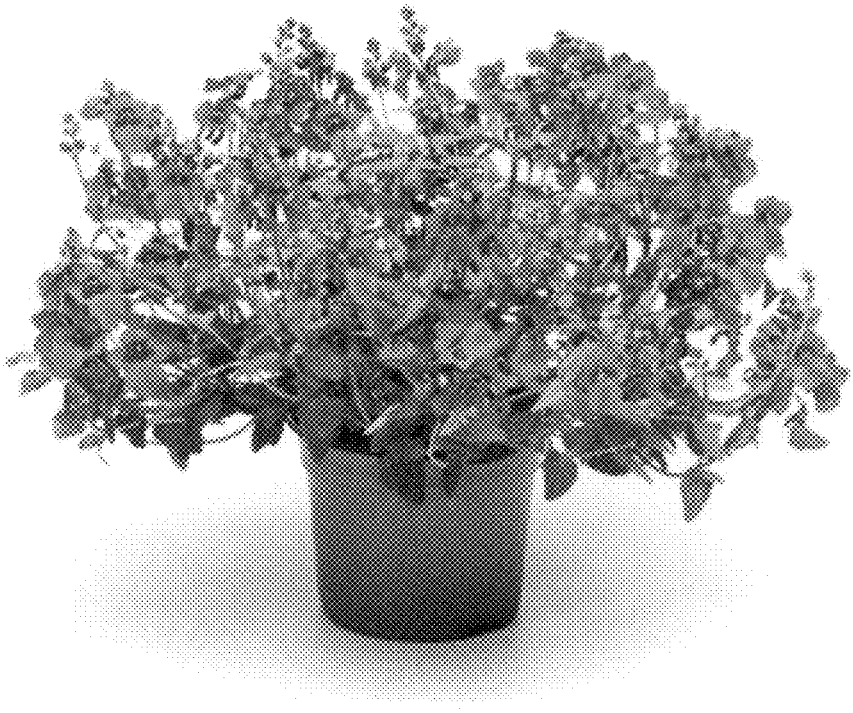
Figure 2:
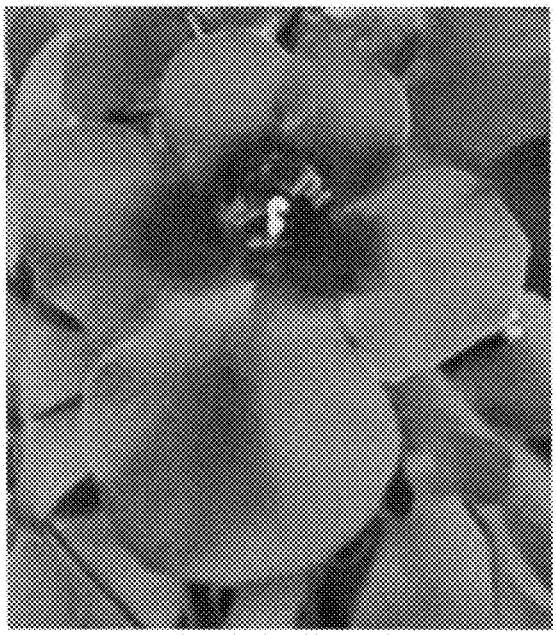

The photographic drawing shows in FIG. 1, a flowering plant of the new variety, and in FIG. 2, a close-up of the flowers.

DETAILED BOTANICAL DESCRIPTION

The aforementioned photographs were taken in mid June 2011 from plants grown in a greenhouse trial in Enkhuizen, Netherlands. These plants were growing in 10.5 cm pots and were approximately 3 months of age.

The plant descriptions and measurements were taken in Andijk, Netherlands in mid May 2011 using 9 week old greenhouse grown plants. Culture of these plants had started in early March 2011, with planting of rooted cuttings into 10.5 cm pots. The young plants received terminal pinches of the apices at about 2-3 weeks after planting.

Color references are made to The Royal Horticultural Society Colour Chart (R.H.S.) 2001.

TABLE 1

DIFFERENCES BETWEEN THE NEW VARIETY 'DISZ0001' AND A SIMILAR VARIETY

| | 'DISZ0001' | 'Diastured' (U.S. Ser. No. 11/375,472, Abandoned) |
|---|---|---|
| Flower color: | RHS 53B | RHS 53C |
| Flower diameter: | 2.2-2.4 cm | 2.2-2.3 cm |
| Plant and growth habit: | Semi-upright | Upright, spreading |

TABLE 1-continued

| DIFFERENCES BETWEEN THE NEW VARIETY 'DISZ0001' AND A SIMILAR VARIETY | | |
|---|---|---|
| | 'DISZ0001' | 'Diastured' (U.S. Ser. No. 11/375,472, Abandoned) |
| Leaf color: | RHS 137A | RHS 138A |
| Leaf margin: | Weakly crenate | More distinctly serrate |

Plant:

*Form, growth and habit*.—Semi-upright, mounded and freely branching.

*Plant height*.—12.0-14.0 cm.

*Plant height* (*inflorescence included*).—19.0-21.0 cm.

*Plant width*.—37.0-39.0 cm.

Roots:

*Number of days to initiate and develop roots*.—7-10 days at about 22 degrees C.

*Type*.—Fine, fibrous, free branching.

*Color*.—RHS N155B but whiter.

Foliage:

*Arrangement*.—Simple and opposite; decussate on non-flowering stems.

*Immature, leaf color, upper surface*.—RHS 137D.

*Lower surface*.—Closest to RHS 138B.

*Mature, leaf color, upper surface*.—RHS 137C.

*Lower surface*.—RHS 138A and RHS 137B.

*Length*.—2.2-2.8 cm.

*Width*.—1.4-1.7 cm.

*Shape*.—Almost triangular.

*Base shape*.—Cordate.

*Apex shape*.—Broadly acute to obtuse.

*Margin*.—Weakly crenate.

*Texture, upper surface*.—Smooth, almost glabrous with sparse, very fine hair.

*Lower surface*.—Glabrous.

*Color of veins, upper surface*.—Indistinct from leaf surface.

*Color of veins, lower surface*.—Closest to RHS 144B.

*Petiole color*.—RHS 137D.

*Length*.—0.2-0.4 cm.

*Diameter*.—0.2 cm.

*Texture*.—Glabrous.

Stem:

*Color of stem*.—RHS 143B to RHS 143C.

*Length of stem*.—24.0-27.0 cm.

*Diameter*.—0.25 cm.

*Length of internodes*.—2.5-4.0 cm.

*Texture*.—Smooth, glabrous.

*Color of raceme*.—RHS 143A.

*Length of raceme*.—6.0-8.0 cm.

*Peduncle raceme*.—0.15-0.2 cm.

*Texture*.—Glabrous.

*Pedicel color*.—RHS 143C.

*Pedicel length*.—1.4-1.5 cm.

*Pedicel diameter*.—0.1 cm.

*Pedicel texture*.—Glabrous.

Inflorescence:

*Type*.—Terminal raceme with flowers in an alternate arrangement at a distance of 0.5-1.0 cm.

*Blooming habit*.—Continuous through the summer months.

*Quantity of inflorescences per plant*.—About 120-160.

*Quantity of flowers per inflorescences*.—Most often 56 open flowers with additional buds.

*Lastingness of individual blooms on the plant*.—3-4 days.

*Fragrance*.—None.

Bud (just when opening/showing color):

*Color*.—RHS 53A.

*Length*.—0.6 cm.

*Width*.—0.5 cm.

*Shape*.—Round to oval.

Corolla:

*Type and shape*.—Single, zygomorphic, salver-shape, 5 petals fused at the base, the two small upper petals mainly fused, two lateral lobes and a broad lower lobe; two short spurs emerge at the underside, formed by the lower ends of lateral and lower petals.

Immature flower:

*Diameter*.—1.9-2.1 cm.

*Color, upper surface*.—RHS 53B.

*Lower surface*.—RHS 53C to RHS 53D.

Mature flower:

*Hortizontal diameter*.—2.2-2.4 cm.

*Vertical height*.—2.3-2.5 cm.

*Depth*.—0.5-0.6 cm.

*Color, upper surface*.—RHS 53B.

*Lower surface*.—RHS 53C to RHS 53D around the outer portions of petals with RHS 53A to RHS 53B in the center of the petals.

*Corolla tube color inside*.—RHS 53A.

*Outside*.—RHS 53C.

*Corolla tube length*.—0.4-0.5 cm.

*Corolla texture, outside*.—Glabrous.

*All lobes, apex*.—Rounded.

*Base*.—Fused.

*Margin*.—Entire.

*Texture*.—Glabrous.

*Upper lobes, length* (*from the corolla opening*).—0.6 cm.

*Upper lobes, width* (*joint*).—1.2 cm.

*Lateral lobes, length* (*from the corolla opening*).—0.7-0.8 cm.

*Lateral lobes, width*.—0.9 cm.

*Lower lobe, length* (*from the corolla opening*).—1.2 cm.

*Lower lobe, width*.—1.7 cm.

Spur:

*Shape and aspect*.—2, short, horn-shaped and downwards directed.

*Spur length*.—0.7-0.9 cm.

*Spur diameter*.—0.3 cm at upper end.

*Spur color*.—RHS 53A.

Calyx:

*Form*.—5 sepals slanting downwards.

*Sepal color*.—RHS 143A.

*Sepal length*.—0.4 cm.

*Sepal width*.—0.2 cm.

*Sepal shape*.—Deltoid.

*Sepal apex*.—Acute.

*Sepal base*.—Fused.

*Sepal texture*.—Glandular hairs.

Reproductive organs:

*Quantity and arrangement*.—4; coherent, arching towards and somewhat twisting around the pistil.

*Filament, color*.—RHS 187A.

*Length*.—0.3-0.4 cm.

*Diameter*.—0.1 cm.

*Anther color*.—RHS 11A.
*Pollen amount*.—Abundant.
*Pollen color*.—RHS 12B.

Pistil:

*Quantity per flower*.—One.
*Length*.—0.4-0.5 cm.
*Stigma color*.—RHS 143D.
*Style color*.—RHS 145C.
*Fertility/seed set*.—Has not been observed on this hybrid.

Disease/pest resistance: Disease/pest resistance has not been observed on this hybrid.

What is claimed is:

1. A new and distinct variety of *Diascia* plant named 'DISZ0001' substantially as illustrated and described herein.

* * * * *